United States Patent
Vilsmeier et al.

(10) Patent No.: US 9,149,655 B2
(45) Date of Patent: Oct. 6, 2015

(54) CONTROLLING A PROCESS OF MONITORING THE POSITION OF A PATIENT DURING A RADIATION TREATMENT

(75) Inventors: Stefan Vilsmeier, Munich (DE); Stephan Erbel, Munich (DE)

(73) Assignee: Brainlab AG, Feldkirchen (DE)

( * ) Notice: Subject to any disclaimer, the term of this patent is extended or adjusted under 35 U.S.C. 154(b) by 265 days.

(21) Appl. No.: 13/634,374

(22) PCT Filed: Mar. 26, 2010

(86) PCT No.: PCT/EP2010/053990
§ 371 (c)(1),
(2), (4) Date: Sep. 12, 2012

(87) PCT Pub. No.: WO2011/116830
PCT Pub. Date: Sep. 29, 2011

(65) Prior Publication Data
US 2013/0006537 A1    Jan. 3, 2013

(51) Int. Cl.
*A61B 6/00* (2006.01)
*A61N 5/10* (2006.01)

(52) U.S. Cl.
CPC ............. *A61N 5/1049* (2013.01); *A61N 5/1067* (2013.01)

(58) Field of Classification Search
CPC .......... A61B 2562/028; A61B 5/0031; A61B 6/507; A61N 5/1037; A61N 5/1048; A61N 5/1049; A61N 5/1067; A61N 5/1071; A61N 2005/1061

USPC ............................ 378/64, 65, 69, 95, 97, 165
See application file for complete search history.

(56) References Cited

U.S. PATENT DOCUMENTS

| | | | |
|---|---|---|---|
| 5,207,223 A | 5/1993 | Adler | |
| 6,118,847 A * | 9/2000 | Hernandez-Guerra et al. | 378/65 |
| 6,144,875 A | 11/2000 | Schweikard et al. | |
| 6,501,981 B1 | 12/2002 | Schweikard et al. | |
| 2007/0201613 A1* | 8/2007 | Lu et al. ............................ | 378/65 |
| 2008/0247510 A1* | 10/2008 | Gertner et al. ................... | 378/65 |
| 2009/0010390 A1* | 1/2009 | Saoudi et al. .................... | 378/97 |

FOREIGN PATENT DOCUMENTS

| | | |
|---|---|---|
| EP | 0 940 158 | 9/1999 |
| EP | 08 169 422.6 | 5/2010 |
| EP | 09 160 153.4 | 5/2010 |

OTHER PUBLICATIONS

U.S. Appl. No. 12/621,881, filed Nov. 1999, Berlinger.
U.S. Appl. No. 12/622,002, filed Nov. 1999, Berlinger.
International Search Report and Written Opinion for International Application No. PCT/EP2010/053990 dated Jun. 28, 2010.

* cited by examiner

*Primary Examiner* — Irakli Kiknadze
*Assistant Examiner* — Juilo M Duarte-Carvajalino
(74) *Attorney, Agent, or Firm* — Tucker Ellis LLP

(57) ABSTRACT

The invention is directed to a method for controlling a process of monitoring the position of at least a part of a patient's body (1) during a radiation treatment, the method comprising the following steps: a) providing an energy value which is dependent on the radiation energy applied to the patient's body (1); b) controlling the time at which the monitoring process is performed, in accordance with the energy value.

22 Claims, 5 Drawing Sheets

CONTROLLING A PROCESS OF MONITORING THE POSITION OF A PATIENT DURING A RADIATION TREATMENT

This application is a national phase of International Application No. PCT/EP2010/053990 filed Mar. 26, 2010 and published in the English language.

The present invention relates to the technical field of monitoring the position of a patient during a radiation treatment, such as for example radiotherapy and/or radio surgery (i.e. radiation surgery) in which a patient is treated by applying radiation to the patient's body. The radiation is in particular an ionising radiation which comprises subatomic particles and/or ions or electromagnetic waves which are energetic enough to ionise atoms or molecules. It is important that the radiation used for the treatment (the "treatment radiation") be effective for particular positions of the body. Movement of the body, in particular relative to a treatment radiation beam, is therefore preferably monitored. The term "treatment radiation" preferably denotes the radiation used to perform the treatment and in particular to achieve a curative effect in a diseased bone and/or diseased tissue. In order to perform the monitoring process, a form of monitoring radiation (for example, x-rays) can be applied to the patient's body. Thus, when for example monitoring using x-rays, the patient is exposed to x-ray radiation as a result of the monitoring process.

Reference is made to the following documents:
U.S. Pat. No. 5,207,223;
U.S. Pat. No. 6,144,875;
U.S. Pat. No. 6,501,981.

The object of the invention is to monitor the position of a patient in a way which represents an optimum compromise between the drawbacks and advantages of monitoring. The invention is in particular directed to improving the quality of radiation treatment. Advantageously, the period of time over which a patient is subject to monitoring and in particular the associated x-ray exposure is minimised, while still ensuring that the treatment radiation effectively hits the desired target.

The aforementioned object is solved by the subject-matter of the independent claims. The dependent claims are directed to advantageous embodiments.

In accordance with one embodiment of the invention, a solution to the aforementioned object is offered by a method for controlling the process of monitoring the position of at least a part of a patient's body during a radiation treatment. This method advantageously comprises a step of providing, in particular determining or receiving an energy value which depends on the radiation energy, in particular the energy of the treatment radiation, which is applied to the patient's body, and a step of controlling the period of time over which monitoring is performed in accordance with said energy value.

In accordance with one embodiment of the aforementioned method, the object is solved by a data processing method. In accordance with this embodiment, the process of monitoring the position of at least a part of a patient's body during a radiation treatment (in particular, radiotherapy and/or radiation surgery) is advantageously controlled by means of a computer, wherein control data are determined in accordance with energy data. The energy data in particular comprise information which describes the (at least one) energy value which depends on the radiation energy applied to the patient's body. This radiation energy can for example be the energy of the treatment radiation and/or monitoring radiation. The control data are preferably designed to control the time, in particular the point in time, at which monitoring is performed. The control data are in particular designed to control the point(s) in time at which monitoring is started and/or ended. Thus, the above-mentioned step of controlling the time at which monitoring is performed is implemented as a step of determining the control data, and the step of providing an energy value is implemented as a step of providing energy data. In the method described in the preceding paragraph, the controlling step can optionally involve issuing control signals. The step of providing the energy value can optionally involve receiving signals (e.g. via an interface) which indicate the energy value and/or measuring the energy value. The step of providing energy data can be implemented as a step of receiving energy data or determining energy data (e.g. based on dose rate and time). The radiation energy is in particular a radiation energy which was applied during a time interval which is prior to the time of the monitoring process which is to be controlled. The monitoring process which is to be controlled is also referred to in this document as the current monitoring process. The time interval can in particular be the time interval from the previous monitoring process to the present time, in particular a point in time prior to the current monitoring process and preferably a point in time immediately preceding a point in time at which a decision has to be made as to whether monitoring is to be performed or not. The previous monitoring process is preferably the last monitoring process, in particular the last monitoring process before the current monitoring process. However, the term "previous monitoring process" can cover not only the last monitoring process but alternatively or additionally any other monitoring process which has been performed before the current monitoring process.

The data processing method is designed to control the process of monitoring the position of at least a part of a patient's body. An example of such a part of the patient's body is in particular a target region which is the target for the radiation treatment and lies in the interior of the patient's body. Exterior and/or outer-surface parts of the patient's body such as the outer surface of the skin can however also form part of a target region. The target region denotes a region of the body to which the radiation used for the treatment is to be applied, in particular in order to achieve a curative effect. Within this context, the term "radiation treatment" denotes procedures such as radiotherapy and/or radiation surgery and/or any other (in particular medical) procedure which uses ionising radiation and in particular applies ionising radiation to at least a part of the patient's body. Alternatively or additionally, however, other body parts—in particular outside the treatment region—can also be monitored in order to determine their position or a shift in their position (in particular, a shift in their position relative to a reference position). For example, movements due to vital functions such as breathing and the pulse and/or heart beat can be monitored. The reference position can for example be determined before the radiation treatment commences. However, it is also possible to determine a reference position during the radiation treatment, for example by performing a monitoring process in accordance with the invention. Preferably, the reference position is determined at an earlier point in time than the point in time at which the position of at least a part of the body is to be monitored.

The expression "monitoring a position" in particular means monitoring a change in the position of the body part in two dimensions or three dimensions. The shift in a tumour due to breathing is for example monitored in two dimensions using two-dimensional x-ray images. Other examples of images which are acquired in order to monitor the position include three-dimensional x-ray images (CT) or magnetic resonance images (MRI) obtained from magnetic resonance tomography (MRT). The radiation used for ascertaining the position of the body part is also referred to in this document as the monitoring radiation. The monitoring radiation advantageously comprises ionising radiation such as electromagnetic radiation and/or waves in the x-ray wavelength range. Monitoring can for example be performed by detecting an internal marker device which is for example located at the position of the target region or at least at a known position relative to the target region. Alternatively or additionally, contrast agents can be used to make the position of the target region visible in the image. An internal marker device preferably comprises a radio-opaque material, such that it can be visually determined in an x-ray image of the body part. An example of an internal marker device is a metal pellet implanted into the prostate or a piece of wire attached to a bone. Alternatively, however, the body part itself can serve as a marker device if its position in an x-ray image or a magnetic resonance image can be determined without using additional marker devices. An example of such a body part is a bone structure and/or a lung tumour which comprises high-density tissue (as compared for example to the surrounding bone structure and/or tissue, respectively) and can therefore be regarded as radio-opaque. Reference is made in this respect to EP 08 169 422.6 and EP 09 160 153.4, which correspond to U.S. Ser. No. 12/621,881 and U.S. Ser. No. 12/622,002, merely by way of example. An external marker device can however also be used. An external marker device is preferably attached to an outer surface of the patient's body, wherein the position of the target region relative to the external marker device is preferably known.

The treatment radiation used for the radiation treatment is in particular ionising radiation which in particular consists of subatomic particles and/or electromagnetic radiation (electromagnetic waves). Using ions and/or atomic particles as the treatment radiation is also within the framework of the invention. The wavelength of the treatment radiation preferably corresponds to x-ray and/or γ-ray wavelengths. The ionising radiation is emitted by an irradiation device such as an x-ray tube and/or a particle accelerator and/or an antenna and/or a radioactive material.

In the method according to the invention, control data are determined in accordance with energy data. The energy data describe an energy value which is in particular calculated from the radiation energy applied to and/or absorbed by at least a part of the patient's body. Generally, the energy value increases with time. The energy value can in particular be reset to a start value (for example, zero). The energy value is in particular reset to the start value when it is determined that the control data are initiating a monitoring process of the patient. The energy data are provided for use by the data processing method. The control data are preferably determined by the computer in conjunction with the monitoring device, wherein the computer and the monitoring device are advantageously operatively coupled together. The control data are preferably determined in accordance with an energy value which fulfills a predetermined condition, i.e. the control data are advantageously adapted to suit a certain energy value. The control data advantageously comprise information on the time, in particular the point in time, at which monitoring is to be performed. In particular, the control data are designed to control when and/or for how long (i.e. for how long a time interval, i.e. the length of time of the monitoring process) monitoring is performed. The control data can for example also comprise information on commands to be issued to the monitoring device, for example a computer tomograph, a conventional x-ray machine and/or a magnetic resonance tomograph. These commands can for example pertain to operating (in particular activating and/or deactivating) the respective monitoring device, i.e. to switching the monitoring device on or off, such that a process of monitoring the position of the body part is performed (started or continued) or is stopped. Accordingly, the control data advantageously comprise a control statement for initiating the monitoring process. Monitoring the position of at least a part of the body in particular includes applying electromagnetic radiation to at least the part of the body, in order to generate data which indicate the position of the body part. Accordingly, the process of controlling the monitoring device in particular comprises the steps of starting and/or ceasing to irradiate the body for monitoring purposes. The expression "irradiating the body" means that at least a part of the body is irradiated. The control data preferably comprise information on when (and how) to monitor the position of at least the part of the patient's body. In particular, the control data comprise information on the radiation energy which has been applied and/or is to be applied to the patient's body or part of the patient's body (in particular, the target region). Preferably, the control data also comprise information on commands which pertain to adjusting the radiation energy which is applied to the patient's body in order to perform a monitoring process (i.e. the radiation energy used for monitoring).

The energy value described by the energy data preferably takes into account properties (such as mass and biological properties) of the irradiated body. The energy data therefore advantageously comprise dose data. The dose data advantageously comprise treatment dose data. Alternatively or additionally, the dose data can comprise monitoring dose data. The treatment dose data describe at least one treatment dose value which is dependent on the radiation energy of the treatment radiation applied to the patient's body. The monitoring dose data describe at least one monitoring dose value which is dependent on the radiation energy of the monitoring radiation applied to the patient's body. The dose data advantageously describe at least one dose value, in particular a radiation dose value, which is dependent on the treatment radiation energy (for example, the energy of the electromagnetic radiation used for the radiation treatment) applied to the patient's body and/or to at least a part of the patient's body. Advantageously, a mass value describing the mass of the patient's body or at least the mass of the irradiated part of the patient's body is known and is used to calculate the dose value which in particular describes the described radiation dose. The dose value is an example of the above-mentioned energy value. The dose value is preferably determined for a time interval which can extend from a previous monitoring process to the present time and/or as a cumulative value over a number of such time intervals (in particular, since the beginning of the current treatment session). Such time intervals are in particular closed intervals, i.e. they have already been completed when the control data are determined. The dose value is for example determined using a dosimeter (which is for example used to measure the energy dose in the vicinity of the patient and/or the irradiating device) or by calculating a dose value on the basis of the known (in particular, predetermined and/or pre-calculated) radiation energy applied. The dose value advantageously denotes an equivalent dose which is applied to the patient's body; it is however, also possible to consider a local dose—applied, for example, to a body part which advantageously comprises the target region—as the dose value.

In accordance with the invention, the dose data can alternatively or additionally be determined on the basis of dose rate data. The dose rate data advantageously comprise information on the dose applied to the patient's body per unit of time (in particular, per unit time interval), preferably since the last interruption in the treatment, in particular since the last radiation treatment session or since the start of the current irradiation treatment session, in particular since the first irradiation during the current treatment session. The dose rate data in particular comprise information on a dose rate applied to the patient's body. The dose rate data advantageously comprise information on a dose which is dispensed within a fixed—in particular, predetermined—time interval. The dose rate data preferably comprise information on a dose applied to at least the part of the patient's body, which is normalised to a standard time interval (a unit of time and/or unit time interval), for example one second, one minute or one hour. The information on the dose per unit of time can be combined with (in particular, multiplied by) time data comprising information on a certain length of time, in particular a length of time which has elapsed during the current treatment session, in order to generate dose data. The monitoring dose data describe at least one dose value which is dependent on the monitoring radiation energy applied to at least a part of the patient's body in order to monitor its position. The monitoring dose is incurred by applying the monitoring radiation.

Advantageously, treatment dose data are alternatively or additionally provided. The treatment dose data advantageously describe at least one dose value, in particular a radiation dose value, which is dependent on the treatment radiation energy (i.e. the energy of the treatment radiation applied to the patient's body). Thus, the respective dose value is a treatment radiation dose value. The dose value is preferably determined for a time interval between the previous monitoring process and the current monitoring process and/or as a cumulative value over a number of such time intervals (in particular, since the beginning of the current treatment session). The dose value is for example determined using a dosimeter (which is for example used to measure the energy dose in the vicinity of the patient and/or the irradiating device) or by calculating a dose value on the basis of the known treatment radiation energy applied. The dose value advantageously denotes an equivalent dose which is applied to the patient's body; it is, however, also possible to consider a local dose—applied, for example, to a body part which advantageously comprises the target region and is irradiated with the treatment radiation energy—as the dose value described by the treatment dose data. One advantage of such a procedure is for example that irradiating the patient's body with an excess of ionising radiation is avoided and that an improved way of reducing the overall dose (in particular, the overall radiation dose) for a patient (comprising the treatment dose and the monitoring dose, in particular the sum of these two) by considering the monitoring radiation and/or the treatment radiation is provided. A decision as to whether to perform monitoring or not can in particular be made on the basis of a determined treatment dose value and/or overall dose value.

In accordance with the invention, the treatment dose data can alternatively or additionally be determined on the basis of treatment dose rate data. The treatment dose rate data advantageously comprise information on the treatment dose applied to the patient's body per unit of time (in particular, per unit time interval), preferably since the last interruption in the treatment, in particular since the last radiation treatment session or since the start of the current radiation treatment session, in particular since the first irradiation with the treatment radiation during the current treatment session. The treatment dose rate data in particular comprise information on the treatment dose rate applied to the patient's body. The treatment dose rate data can also comprise information on a treatment dose which is dispensed within a fixed—in particular, predetermined—time interval. The treatment dose rate data preferably comprise information on a treatment dose applied to at least the part of the patient's body, which is normalised to a standard time interval, for example one second, one minute or one hour. The information on the treatment dose per unit of time can be combined with (in particular, multiplied by) time data comprising information on a certain length of time (in particular, a length of time which has elapsed during the current treatment session) in order to generate treatment dose data.

Preferably, the control data comprise information relating to controlling the monitoring process when the energy value described by the energy data reaches a threshold value (an energy threshold value, in particular a dose threshold value). One advantage of controlling the monitoring process in accordance with the radiation energy applied is that monitoring can for example be performed more often when using high treatment radiation energies than when applying lower treatment radiation energies, thereby avoiding major radiation damage from irradiation with high radiation energies, for example if tissue outside the target region is irradiated. The threshold value can be dependent on the treatment dose reaching a threshold value (a treatment threshold value) and/or on the monitoring dose reaching a threshold value (a monitoring threshold value). The distribution over time of the monitoring processes is thus simplified, while still being able to keep the overall radiation dose low. The threshold value can be predetermined or variable. A variable threshold value can be adequate if the treatment radiation energy is varied during the treatment. If, for example, a higher treatment radiation energy is applied for a certain time interval, the threshold value can be increased such that the time interval between monitoring processes remains constant or at least approximately constant, even though a lower treatment radiation energy is applied during other time intervals. The threshold value can be decreased if the patient moves a lot during the radiation treatment, in order to avoid damage to body parts which are not meant to be irradiated, in particular irradiated with the treatment radiation. These conditions or variations regarding the threshold can be applied independently of or in combination with other conditions, which are described below. A decision as to whether the monitoring device is to be controlled in a certain way as described above is advantageously based on balancing a need for additional monitoring (caused for example by the patient moving) with the risk of causing unnecessary radiation damage.

In accordance with the invention, the threshold value can be predetermined (in particular, fixed) or variable in accordance with different factors. The threshold value can for example vary in accordance with the state of the patient's health. To this end, the threshold value can vary in accordance with patient data describing the patient's state of health. The state of health can be described by variables such as blood pressure and/or heart beat frequency and/or the number of certain blood constituents (such as for example leucocytes) and/or data comprising information about administered drugs. Alternatively or additionally, the threshold value can vary in accordance with treatment data which describe the type and/or status of the disease which is to be treated by the radiation treatment. The type of disease can for example be identified by data which comprise information on the body region in which a tumour and/or tissue to be irradiated is situated. The status of the disease can for example be characterised by data which comprise information on for example the progression of tumour growth or on whether any promising changes due to the radiation therapy have been determined so far.

Alternatively or additionally, the threshold value can vary in accordance with beam data which describe a radiation beam used for radiotherapy, in particular the path of the beam and/or the direction of the beam. The beam data can in particular comprise information about the geometry of the beam which is used for the radiation treatment. Preferably, the threshold value is decreased for a fanned and/or conical beam geometry, while for a tubular and/or highly resolved beam geometry (in particular, parallel rays having a low overall diameter), a higher threshold value can be envisaged. Preferably, the threshold value is decreased if the beam data indicate that the treatment radiation beam is close to healthy body parts which the treatment radiation is to be kept away from.

Alternatively or additionally, the threshold value can vary in accordance with the dose data. The threshold value can for example be adapted to a dose value which has already been reached. By analogy, the threshold value can vary in accordance with the treatment dose data reaching a treatment threshold value and/or the monitoring dose data reaching a monitoring threshold value. The threshold value for the treatment dose can for example be decreased if a large treatment dose has been determined, thus avoiding excessive radiation damage. Thus, the threshold value can be determined by an interdependency of the overall dose and/or treatment dose and/or monitoring dose. This dependency can advantageously be used to limit the overall dose by taking into account the monitoring dose, which is itself dependent on the monitoring processes. The contribution by the monitoring radiation to the overall radiation dose can thus be minimised. Irradiation with monitoring radiation and/or treatment radiation can for example be stopped if one or more of the different dose values reach(es) its threshold value. This is in particular useful if the monitoring radiation dose appears to be easier to control than the treatment radiation dose. In particular, an operator and/or the navigation system can decide whether or not to perform monitoring in accordance with whether a shift in the position of at least a part of the patient's body is detected (advantageously, using movement indication data as described below). The application of treatment radiation, by contrast, can be essential for a successful radiation treatment and thus more difficult to vary. The monitoring dose data can also be normalised to a certain time interval, in the same way as the treatment dose rate data. Such time-normalised monitoring dose data are referred to as monitoring dose rate data.

Alternatively or additionally, the threshold value can vary in accordance with monitoring dose rate data (in particular, monitoring radiation dose per unit of time data) which describe the radiation dose applied to the patient's body by monitoring radiation per unit of time (in particular, per unit time interval). The term "monitoring dose rate data" is defined in the same way as the terms "dose rate data" and/or "treatment dose rate data". Thus, the monitoring dose rate data in particular comprise information on a monitoring dose rate which is applied to the patient's body. If the threshold value varies in accordance with the monitoring dose rate data, the threshold value can be adapted such that monitoring is for example stopped if a certain normalised radiation dose per standard unit of time (for example one second, thirty seconds or one minute), advantageously a certain value of the treatment dose and/or monitoring dose, is reached. This feature helps to avoid the patient receiving a large equivalent and/or local dose within a short amount of time and can therefore also help to avoid injury which may for example resulting in burns and/or radiation sickness.

Alternatively or additionally, the threshold value can vary in accordance with movement indication data which describe a frequency and/or degree of movement of the patient's body. The movement indication data can be determined on the basis of at least one of: a vibration measurement of the patient's body; a vital parameter of the body; a comparison with preceding monitoring results; and/or an optical analysis of the movement of the body. In particular, a marker device (as described below) can be attached to the body in order for the movement of the body to be detected by means of a navigation system, thereby generating movement indication data. A vibration measurement can be performed in order to determine minor movements of at least a part of the patient's body which can be caused by a tremor which is for example common in patients suffering from Morbus Parkinson or other similar neurological diseases. The vital parameter used to determine the movement indication data can for example be the heart beat frequency and/or blood pressure and/or breathing frequency which can for example be used to characterise the movement of the heart and/or other organs, in particular the thoracic and/or abdominothoracic organs. The movement indication data can for example be determined by irradiating the relevant parts of the patient's body (in particular, exterior parts) with optical light such as a visible laser beam and detecting the reflection of said beam off the patient's body. A movement frequency of the patient's body is preferably determined for cyclic movements of the body such as tremors. The movement indication data preferably also comprise information on a history and/or chronological series of positions of the patient's body. To this end, the current monitoring result (i.e. the determined position) is compared with preceding and/or previous monitoring results (i.e. previously determined positions), wherein a tendency (in particular, a temporal and/or spatial tendency) of the movement of the patient's body can be determined and used to control the direction and/or intensity of the treatment radiation beam. The dependence of the threshold value on the movement indication data can be useful in order to avoid applying treatment radiation above a certain equivalent dose and/or a certain local dose to body regions which are not to be irradiated. This can be helpful in ensuring that a for example anxious or agitated patient is not negatively affected by the radiation.

In accordance with the invention, the treatment dose data can be determined on the basis of time data and in particular calculated using time data which comprise information on the time which has elapsed since a previous monitoring process or since a previous radiation treatment session. The time data can also comprise information on an absolute time which can for example be used in order to perform monitoring at a predetermined time, in particular a clock time and/or a time defined within a global timeframe. Such a measurement of time can also be denoted as an "absolute time" within the framework of this invention.

The invention also discloses a method for controlling a process of monitoring the position of at least a part of a patient's body during a radiation treatment, in particular radiotherapy and/or radiation surgery. The features of the method in accordance with the invention for controlling a monitoring process are analogous to the features of the data processing method for controlling a monitoring process, as described above.

The invention also discloses a radiation treatment system. The radiation treatment system comprises a computer which is designed to determine energy data and to issue control data for controlling a monitoring device. The computer preferably determines the energy data in accordance with the above-mentioned data processing method for controlling a monitoring process and/or the above-mentioned method for controlling a monitoring process. The radiation treatment system also preferably comprises a monitoring device which is designed to monitor the position of at least a part of the patient's body which is to be treated using the treatment radiation. The monitoring device is preferably controlled in accordance with the control data. The type of monitoring device used is preferably dependent on the type of monitoring radiation which is to be applied in the monitoring process. Thus, the monitoring device can for example be a common x-ray machine, a computer tomograph or a magnetic resonance tomograph. The radiation treatment system also preferably includes an irradiation device which is designed to emit the treatment radiation used for the radiation treatment. The computer is advantageously also designed to collect treatment dose rate data from the irradiating device. The computer is also advantageously designed to collect monitoring dose rate data from the monitoring device.

The present invention relates to a corresponding method, data processing method, program, program product, computer, signal wave and radiation treatment system. The method in accordance with the invention is in particular a data processing method. The data processing method is preferably performed using technical means, in particular a computer. The computer in particular comprises a processor and a memory in order to process the data, in particular electronically. The determining or calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion.

Computer program elements of the invention can be embodied by hardware and/or software (including firmware, resident software, micro-code, etc.). The computer program elements of the invention can take the form of a computer program product which can be embodied by a computer-usable or computer-readable storage medium comprising computer-usable or computer-readable program instructions, "code" or a "computer program" embodied in said medium for use by or in connection with the instruction-executing system. Such a system can be a computer; a computer can be a data processing device comprising means for executing the computer program elements and/or the program in accordance with the invention. Within the context of this application, a computer-usable or computer-readable medium can be any medium which can contain, store, communicate, propagate or transfer the program for use by or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s). The computer and/or data processing device can in particular include a guidance information device which includes means for outputting guidance information, in particular a guidance signal. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

A marker device, in particular an external marker device, can for example be a reference star or a pointer or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

It is the function of a marker device to be detected by a marker detection device (for example, a camera or an ultrasound receiver), such that its spatial position (i.e. its spatial location and/or alignment) can be ascertained. The detection device is in particular part of a navigation system. The marker devices can be active marker devices. An active marker device can for example emit electromagnetic radiation and/or waves, wherein said radiation can be in the infrared, visible and/or ultraviolet spectral range. The marker device can also however be passive, i.e. can for example reflect electromagnetic radiation in the infrared, visible and/or ultraviolet spectral range. To this end, the marker device can be provided with one or more markers having a surface which has corresponding reflective properties. It is also possible for a marker device to reflect and/or emit electromagnetic radiation and/or waves in the radio frequency range or at ultrasound wavelengths. A marker of a marker device preferably has a spherical and/or spheroid shape and can therefore be referred to as a marker sphere; markers can also, however, exhibit a cornered—for example, cubic—shape.

A "reference star" refers to a marker device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of marker devices to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the marker devices to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the data processing method of the invention. Preferably, the navigation system comprises a detection device (i.e. the marker detection device described above) for detecting the position of markers (of a marker device) and supplying the detection signals generated to the computer, such that the computer can determine the position of the markers (and therefore of the marker device) on the basis of the detection signals received. The positions of the markers (of a marker device) can for example be detected in a spatial reference frame (a co-ordinate system) which can advantageously be centered at the position of the detection device. It is however also possible in accordance with the invention to centre the reference frame at another location which advantageously lies within the field of view of the detection device. The field of view advantageously consists of all the positions which can be detected by the detection device, in particular when the detection device is arranged in a certain spatial setup. Thus, the positions of the markers (and therefore of the marker device) can be determined relative to the position of the detection device. The navigation system also preferably comprises a user interface for receiving the calculation results from the computer. The user interface provides the received data to the user as information. Examples of a user interface are a monitor or a loudspeaker. The user interface can use any kind of indication signal (for example a visual signal, an audio signal and/or a vibration signal).

Data used to perform the method in accordance with the invention are advantageously provided to the method as described in the following.

Where data, regions, ranges or images are "provided", this means that they are ready for use by the method in accordance with the invention. The data, regions, ranges or images can achieve this state of being "provided" by for example being detected or captured (for example by analysis apparatus such as the monitoring device and/or the computer of the present invention) or by being inputted (for example via interfaces). The data can also achieve this state by being stored in a memory (for example a ROM, CD and/or hard drive) and thus ready for use within the framework of the method in accordance with the invention. The data can also be provided by being calculated on the basis of other data. For example, the energy data are provided to the method in accordance with the invention by being calculated on the basis of inputted time data and dose rate data. Known operating data of the device(s) used to emit the treatment radiation and/or monitoring radiation can for example be used for this purpose. The latter data can be received from the treatment device. The energy data can alternatively or additionally be provided by a dosimeter, etc.

Where data are "provided", this means that they are ready for use by the method or program in accordance with the invention. The data can achieve this state of being "ready for use" by for example being generated, in particular detected or captured (for example by analysis apparatuses) or by being input (for example via interfaces). The data can also achieve the state of being provided by being stored in a data storage (for example a ROM, RAM, CD and/or hard drive) and thus ready for use within the framework of the method or program in accordance with the invention. The expression "providing data" encompasses (within the framework of a data processing method) in particular that the data are determined by the data processing method or program. The meaning of "providing data" in particular encompasses that the data are received by the data processing method or program, in particular to further process the data by the data processing method or program. Thus "providing data" can mean for instance to wait for a reception of data and to receive the data. The received data can be for instance inputted by the interface. "Providing data" can also mean that the data processing method or program performs steps to (actively) acquire the data from a data source, for instance a data storage (for instance ROM, RAM, data base, hard disk etc.) or via the interface (for instance from another computer or a network).

The above-mentioned features of the invention are described in more detail by the following embodiments which are to be regarded merely as examples and do not limit the invention, wherein.

Figure 1A:
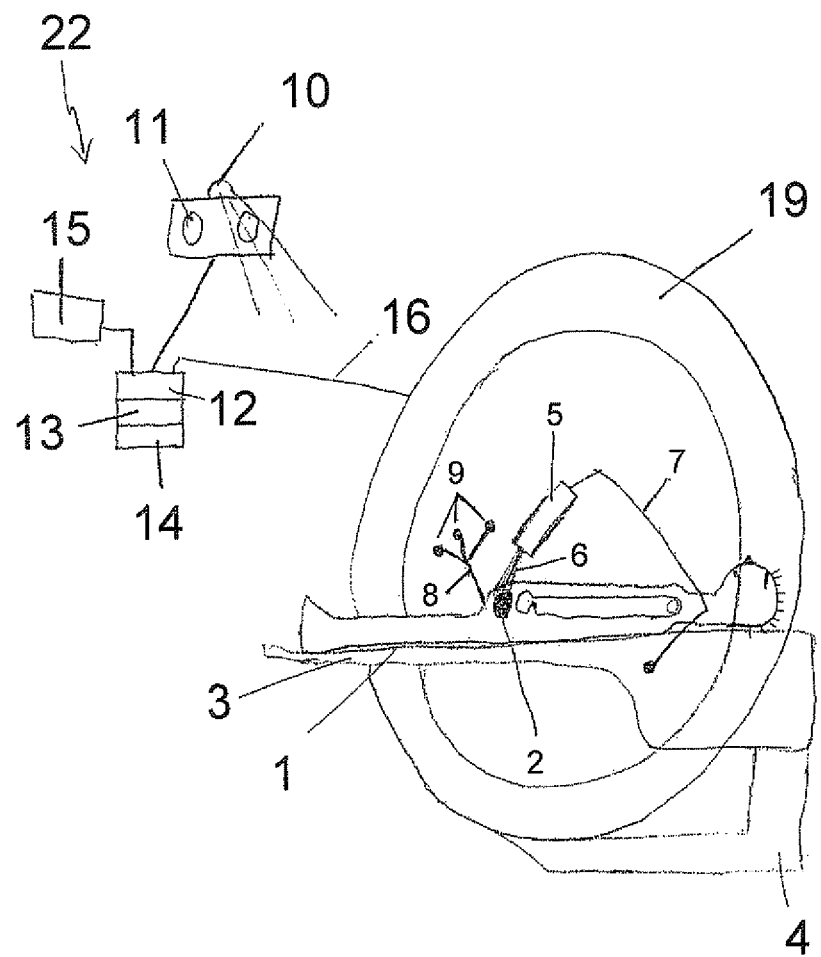
FIGS. 1a and 1b show a setup respectively according to a first and second embodiment used for performing radiotherapy and monitoring the patient's position in accordance with the invention.
Figure 1B:
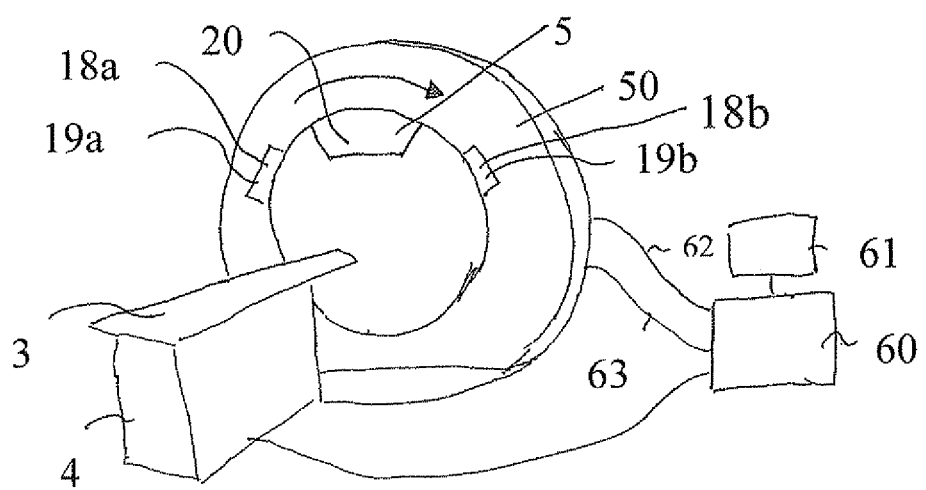
Figure 2:
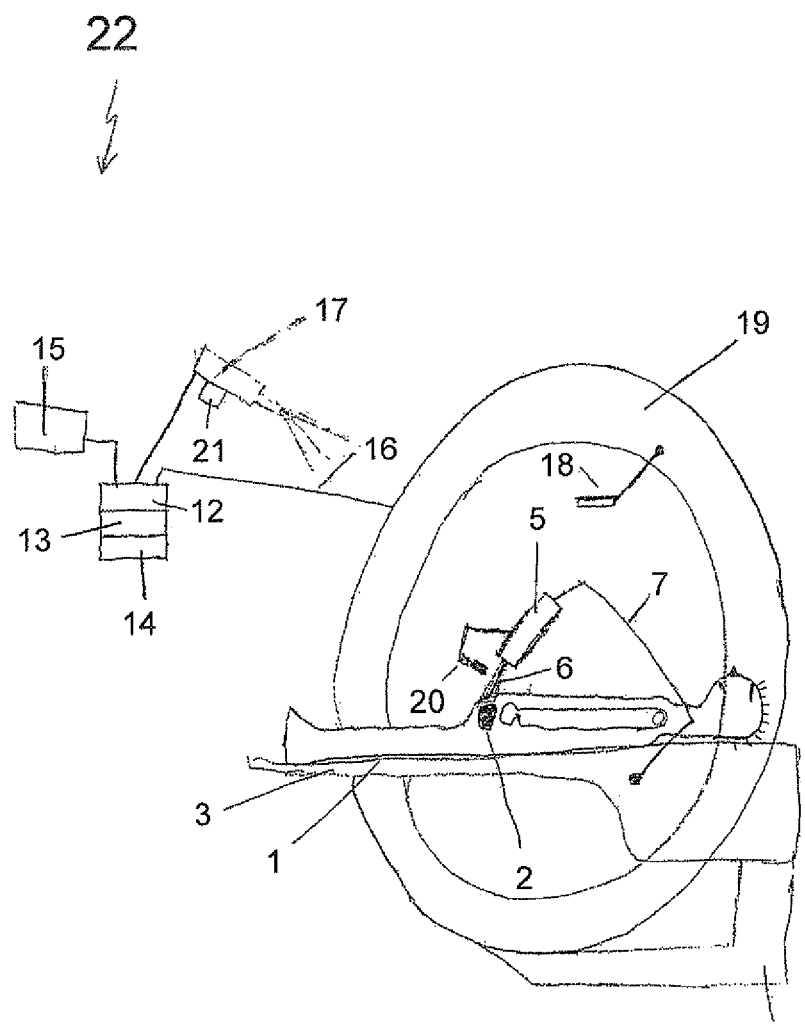
FIG. 2 shows an alternative embodiment for an optical analysis of the movement of the patient's body.

FIG. 1 shows a radiation therapy setup in accordance with a first embodiment, comprising a table 3 onto which the patient 1 is placed. The table 3 is preferably movably coupled to a stand 4. The table 3 can be moved to a fixed and/or predetermined position relative to a monitoring device 19 which can share the stand 4 with the table 3. The monitoring device 19 can comprise a computer tomograph or a camera for producing stereographic x-ray images (i.e. an x-ray machine, preferably comprising two x-ray emitters). A region of interest 2, such as for example a target region, within the patient's body is to be irradiated with treatment radiation 6. The treatment radiation 6 is preferably emitted by an irradiation device such as the treatment device 5 which can be moved to a defined position relative to the region of interest 2. As described with respect to FIG. 1b, the treatment device can comprise a support structure which exhibits the same size as the ring of the monitoring device 19 as shown in FIG. 2 and supports a movable irradiation device. The irradiation device can also be supported by movable robot arms. In the example shown in FIG. 2, the irradiation device is held in a container which is attached for example relative a movable arm 7. The treatment device 5 can comprise a suitable radioactive substance or a source of x-rays, preferably hard x-rays, or a particle accelerator. The movable arm 7 can be mechanically coupled to the table 3, such that a common reference system comprising the table 3, the treatment device 5, the monitoring device 19 and the patient's body 1 is formed.

The monitoring device 19 and/or the treatment device 5 is/are operatively coupled by a data link 16 (such as a data cable and/or a radio link) to a navigation system 22 which comprises a processor (CPU) 12, a volatile memory such as a RAM 13 and a permanent memory such as a hard disc 14. In the navigation system 22, an electromagnetic emitter 10 such as an emitter for infrared and/or ultraviolet radiation and a stereotactic camera 11 which is sensitive to the respective electromagnetic radiation are used to ascertain the position of a reference star 8. The reference star 8 comprises markers 9 and is preferably attached to the patient's body 1. In particular, the position of the reference star 8 relative to the region of interest 2 is defined and known. The navigation system 22 also comprises a display 15 which can be used to display data relating to the radiotherapy procedure and/or to visualise a graphic model of the region of interest 2.

The CPU 12, the RAM 13 and preferably the hard disc 14 advantageously form part of the computer of the navigation system 22. This computer can determine a monitoring dose dispensed by the monitoring device 19 to the patient's body 1 and/or the region of interest 2. This determination can be based on known values of the x-ray energy emitted by the monitoring device 19 and for example on data comprising information on the mass of the region of interest 2 and/or the patient's body 2. The computer can also be used to determine the time which has elapsed during the radiation treatment (for example by using an internal clock) and can be provided with data comprising information on the radiation energy emitted by the treatment device 5 to the region of interest 2 and/or the patient's body 1. Such data are referred to as treatment dose data within the framework of this invention. The computer can then use the treatment dose data to issue control data to the monitoring device 19 in order to perform a data processing method for controlling the monitoring process, as described above. The monitoring device 19 is used to determine the position of the region of interest 2 and/or other parts of the patient's body 1. The position of the reference star 8 and therefore also of the region of interest 2 determined by the navigation system 22 can be used as a cross-check for the position determined from the x-ray images produced by the monitoring device 19. The positions determined by the two devices can be compared and evaluated for possible deviations.

FIG. 1b shows an alternative radiationship therapy setup. The treatment device 5 is rotatable along a ring 50. A table 3 is movably coupled to the ring 50. The patient can be placed on the table 3. The table 3 is preferably movably coupled to a stand 4. There are two monitoring devices 19a and 19b. The irradiation device 5 preferably emits the treatment radiation towards the center of the ring 50. A treatment dosimeter 20 can be part of the treatment device 5 and is in particular located in the head of the treatment device 5 which emits the treatment radiation. Accordingly also the monitoring dosimeter 18a and 18b can be respectively located in the monitoring devices 19a and 19b. The monitoring dosimeter 18a and 18b and/or the treatment dosimeter 20 can be of any standard types such as for example a film dosimeter and/or geiger counter. A computer 60 includes preferably a CPU, a RAM, and a harddisc as well as a laser screen 61. The computer receives signals representing the monitoring signals as well as dose data from the monitoring dosimeters 18a and 18b as well as the treatment dosimeter 20 via a line 62. The monitoring and the radiation treatment is controlled via a line 63 by means of the computer 60. Preferably, the data processing method according to the invention is running on the computer 60. The computer 60 can also control the navigation system 22 as described with respect to FIG. 1a. The navigation system 22 can also be part of the setup described with respect to FIG. 1b.

The embodiment shown in FIG. 2 is similar to the embodiment of FIG. 1a, with the exception that the position of the patient's body 1 and any movement of the patient's body 1 during the radiation therapy is ascertained using a light source 17 which is operatively coupled to the computer. The light source 17 can for example emit a coherent and collimated light beam such as a laser beam (preferably, a laser beam in the visible light range). The light beam is irradiated onto the patient's body 1 and/or onto a surface area of the patient's body 1 which preferably represents a projection of the region of interest 2 onto the surface of the body. The reflection of the light beam from the patient's body 1 is detected by a sensor 21 which can for example be a CCD (a charge-coupled device). The reflection can in particular be used to identify a small-scale movement of the region of interest 2, in particular relative to the treatment radiation source 5 (the position of which relative to the region of interest 2 and/or the light beam is preferably known).

The treatment radiation dose is determined by a treatment dosimeter 20, and the monitoring radiation dose is determined by a monitoring dosimeter 18. The monitoring dosimeter 18 can be placed in the vicinity of the monitoring device 19 and/or the region of interest 2 and/or the patient's body 1. The location of the monitoring dosimeter 18 relative to the other entities mentioned can be dependent on the quality of the treatment dose data to be achieved and on the type and/or position of the treatment device 5 and/or the position and/or type of the region of interest as well as on other practical considerations within the framework of for example handling the patient. Similarly, the treatment dosimeter 20 is advantageously placed in the vicinity of the treatment device 5 and/or the region of interest 2. The monitoring dosimeter 18 and/or the treatment dosimeter 20 can be of a standard type such as for example a film dosimeter and/or a Geiger counter.

The signals generated by the dosimeters 18, 20 can be read by the computer of the navigation system 22. The treatment dose data are determined on the basis of the signals generated in the treatment dosimeter 20, and the monitoring dose data are determined on the basis of the signals generated in the monitoring dosimeter 18.

The treatment dosimeter 20 and the monitoring dosimeter 18 are operatively coupled, for example by a data link 16, to the navigation system 22, such that the computer of the navigation system 22 can determine treatment dose values and monitoring dose values from the signals generated in the dosimeters 18, 20. The dose values determined are embodied by dose data and/or treatment dose data and/or monitoring dose data. Dependent on these data reaching respective threshold values, the computer controls the monitoring device 19 to start and/or stop emitting x-rays in order to produce x-ray images for determining the position of at least a part of the patient's body 1, i.e. the computer controls the monitoring process in the sense of this invention.

The optical analysis of the movement of the body by the stereotactic camera 11 and light source 17 as shown in FIGS. 1 and 2, respectively, can be used as a cross-check for the position of the region of interest 2 and/or the position of the patient's body 1 as determined from the x-ray images generated using the monitoring device 19. However, the method in accordance with the invention can also be performed without such a cross-check, in which case the method steps relating to controlling the monitoring device 19 and/or the treatment radiation source 5 can be executed by a computer which in general comprises a processor, a volatile memory and preferably a non-volatile memory as described above. It can then be unnecessary to use a navigation system which in particular ascertains positions of the region of interest 2 and/or the patient's body 1 by optically determining them. The positions can then be determined from the x-ray images produced by the monitoring device 19, preferably using internal and/or external markers as described above.

Figure 3:
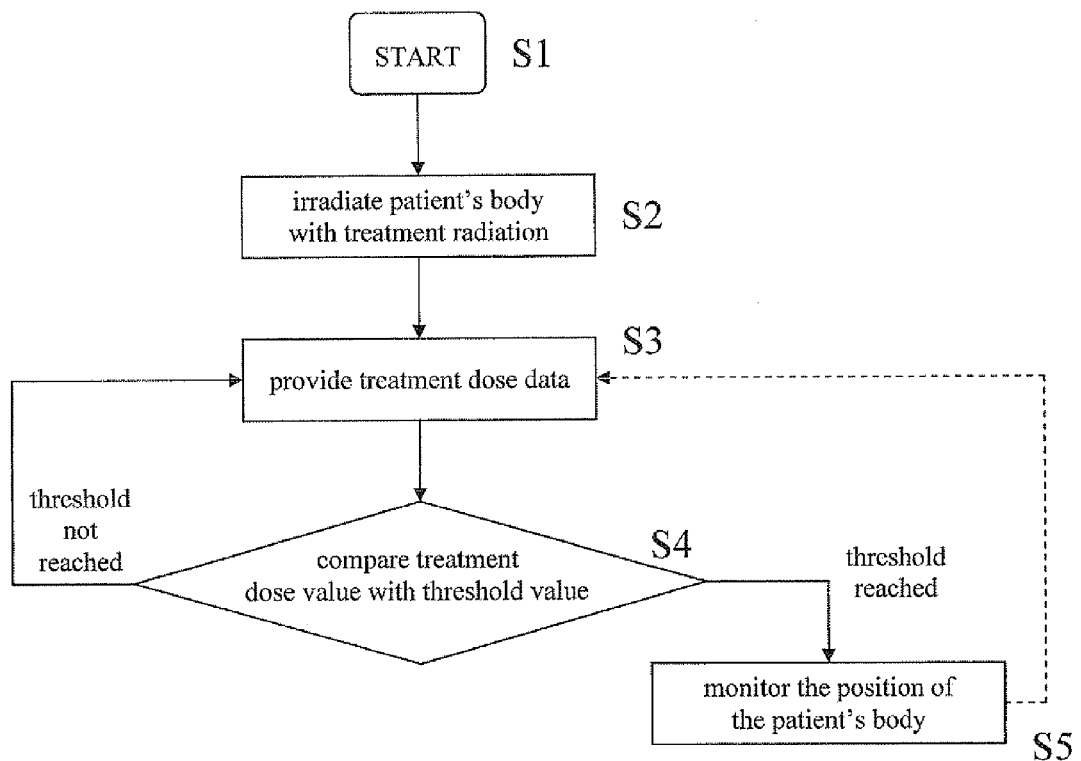
FIG. 3 shows a flow diagram of steps of a first embodiment of a method in accordance with the invention.

FIG. 3 is a flow diagram which describes steps of a first embodiment of a method in accordance with the invention. In step S1, the radiation treatment is started for instance by pressing a button on the computer 60 shown in FIG. 1b. In step S2, the treatment device 5 starts with emission of the treatment radiation. A treatment dosimeter 20 measures the treatment dose and issues data describing the treatment dose to the computer 60. In step S3, the computer 60 receives the data from the dosimeter 20, so that the treatment dose data are provided in step S3. Preferably, if the step S3 is re-entered later, the computer 60 determines the treatment dose data to describe the dose value since the previous monitoring took place. For instance, a difference between the current dose value received from the dosimeter 20 and the dose value at the time of the previous monitoring is calculated. The calculated difference represents the provided treatment dose value which is to be compared with the threshold value. This step of comparison is step S4 and is preferably performed by the computer 60. If the threshold is not reached, the process returns to step S3 in order to receive or determine the current dose value which in particular has increased due to the continued emission of the treatment radiation. If the comparison step S4 determines that the dose value has reached the threshold value, then the computer determines control data which control the monitoring device 19 (19a and 19b in FIG. 1b) to monitor the position of the patient's body. Then the method returns to step S3. Preferably, in step S3, the dose value at the time of monitoring is stored in order to be able to calculate from now on the dose value by calculating the afore-mentioned difference between the current dose value and the dose value at the time of the previous (most recent) monitoring.

Figure 4:
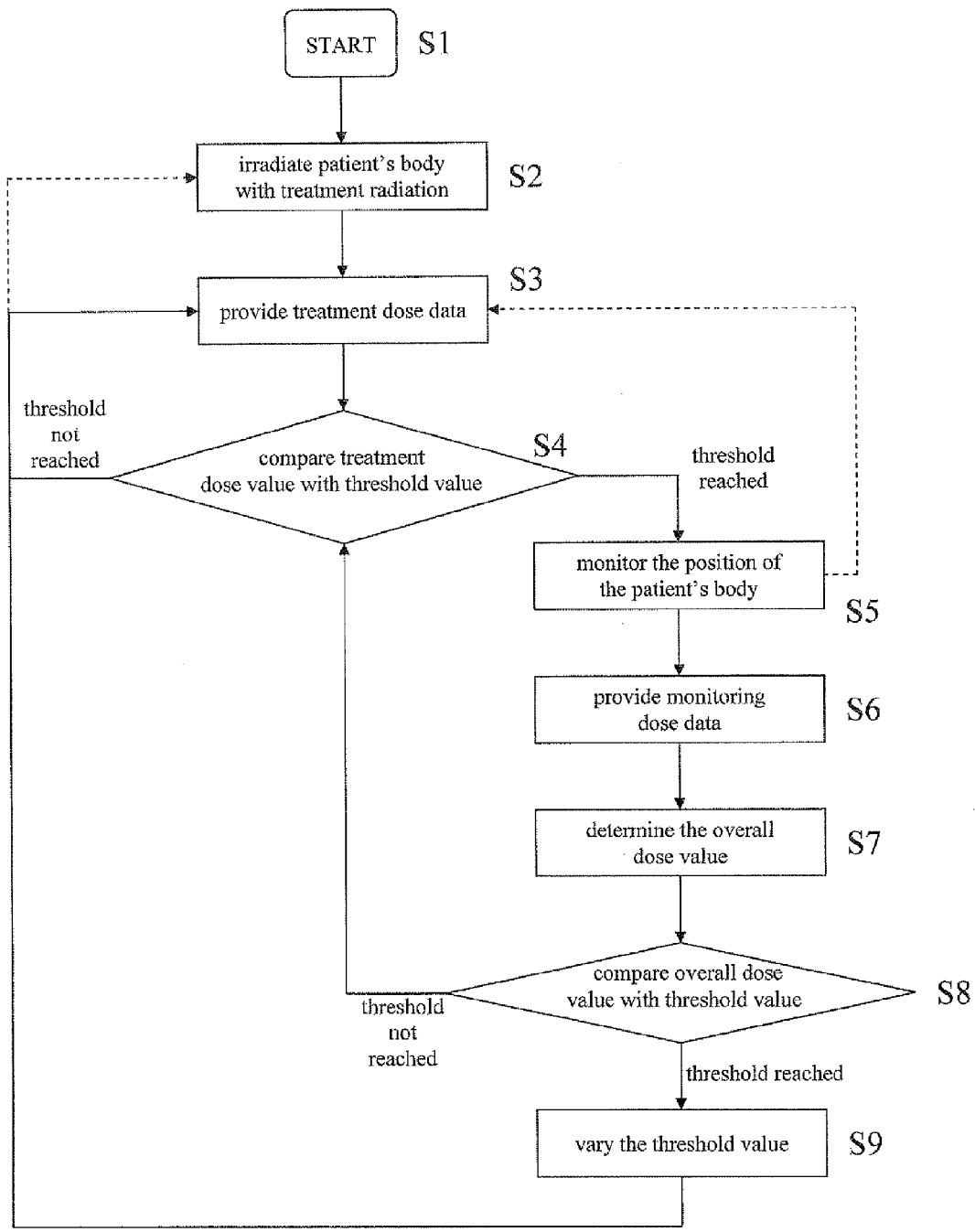
FIG. 4 shows a flow diagram of steps of a second embodiment of a method in accordance with the invention.

FIG. 4 is a flow diagram which describes steps of a second embodiment of a method in accordance with the invention. In Step S1, a radiation treatment is started, for example by retrieving a procedure for a monitoring device 19, a treatment device 5 and dosimeters 18 such that they are set to an active state and ready to perform the method in accordance with the invention. In Step S2, the treatment device 5 is controlled in such a way that a patient's body 1 (or at least a part of it) is irradiated with treatment radiation. In Step S3, treatment dose data are then provided by the treatment device 5 or are for example determined by the dosimeter 20. In Step S4, the treatment dose value described by the treatment dose data is compared, preferably with a treatment threshold value. Preferably, the treatment dose data describe the dose value since the most recent monitoring took place. If it is determined in Step S4 that the treatment dose value has not reached the threshold value, the method returns to Step S3 and continues to provide or determine the treatment dose data. Alternatively, the method can return to Step S2 and continue to irradiate the patient with the treatment radiation, if irradiating with the treatment radiation was interrupted in order to provide or determine the treatment dose data. If it is determined in Step S4 that the treatment dose value has reached the threshold value, i.e. that the treatment dose value is larger than or equal to the threshold value, the method continues by monitoring the position of the patient's body (or at least the part of the patient's body which is to be irradiated with the treatment radiation) in Step S5. In particular, when the threshold is reached and monitoring is activated (S5), the treatment dose data are resetted when the method goes from S5 to S3, so that treatment dose data (provided in S3) describe the dose value accumulated since the most recent monitoring took place. The threshold value is preferably varied in accordance with a degree of movement of the position of the patient's body, as determined in Step S5. The threshold value is for example decreased if a large degree of movement is determined, and can be increased or left unchanged if a small degree of movement is determined. In one embodiment of the method, Step S5 can be followed by an evaluation as to whether the patient's body is at the desired position for performing the radiation treatment. If this is the case, the method can return to Step S3. If, however, it is determined that the patient's body is not lying at the desired position, then the radiation treatment can be interrupted or stopped. In accordance with FIG. 4, Step S5 is followed by Step S6 in which monitoring dose data are provided, preferably by the monitoring device 19. Alternatively, the monitoring dose data can be provided by the dosimeter 18. In Step S7, the overall dose value is then determined by adding the treatment dose value to the monitoring dose value. In Step S8, the overall dose value is compared with the overall threshold value. If it is determined in Step S8 that the overall dose value has not reached the overall threshold value (i.e. the overall dose value is less than the overall threshold value), the method returns to Step S4. If however, it is determined in Step S8 that the overall dose value has reached the overall threshold value (i.e. the overall dose value is more than or equal to the overall threshold value), then the method according to FIG. 4 continues at Step S9 in which the threshold value (i.e. at least one of the treatment threshold value, the monitoring threshold value and the overall threshold value) is varied in accordance with the conditions of the present radiation treatment, as described above. Once the threshold value has been varied, the method continues either at Step S3 or Step S2, depending on whether or not irradiating with the treatment radiation was interrupted before initiating Step S3. Alternatively, if it is determined in Step S8 that the overall dose value has reached the overall threshold value, the radiation treatment can be interrupted or stopped in order to avoid excessive radiation damage.

Features of the invention from different embodiments as described above can also be combined where this is technically expedient and/or feasible.

The invention claimed is:

1. A method for controlling a time of performing a next process of monitoring the position of at least a part of a patient's body during a radiation treatment, ionizing radiation being applied to the patient's body during radiation treatment, the applied ionizing radiation having a radiation energy, the method comprising the following steps:
   a) providing an energy value which is dependent on the radiation energy applied to the patient's body since a previous monitoring process; and
   b) controlling the time at which the next monitoring process is performed in dependence on when the energy value reaches a threshold value.

2. A data processing method for controlling a process of monitoring the position of at least a part of a patient's body during a radiation treatment by means of a computer, the data processing method comprising the steps of the method of claim 1, wherein energy data are provided which describe the energy value, and control data are determined in accordance with the energy data, wherein the control data are designed to control the time at which monitoring is performed.

3. The data processing method according to claim 2, wherein the energy data comprise dose data, and the energy value is a dose value which quantifies a radiation dose.

4. The data processing method according to claim 3, wherein the dose data comprise treatment dose data which describe at least one dose value which is dependent on the treatment radiation energy applied to at least a part of the patient's body.

5. The data processing method according to claim 4, wherein the treatment dose data are determined on the basis of time data which describe the length of time of the radiation treatment and on the basis of treatment dose rate data which describe a treatment dose which is applied to the patient's body per unit of time.

6. The data processing method according to claim 4, wherein the dose data comprise monitoring dose data which describe at least one dose value which is dependent on the monitoring radiation energy applied to at least a part of the patient's body.

7. The data processing method according to claim 6, wherein the monitoring dose data are determined on the basis of time data which describe the length of time of the monitoring process and on the basis of monitoring dose rate data which describe the monitoring radiation energy applied to the patient's body per unit of time.

8. The data processing method according to claim 2, wherein the radiation energy is the radiation energy which has been applied to at least a part of the patient's body since a previous monitoring process.

9. The data processing method according to claim 2, wherein threshold data are provided which describe a threshold value, and the control data include a control statement for initiating the monitoring process when the energy value described by the energy data reaches the threshold value.

10. The data processing method according to claim 9, wherein the threshold value is predetermined or variable.

11. The data processing method according to claim 9, wherein the threshold value varies in accordance with:
 a) patient data which describe the state of the patient's health; and/or
 b) treatment data which describe the type and/or status of the disease which is to be treated by the radiation treatment; and/or
 c) beam data which describe a radiation beam used for radiotherapy; and/or
 d) monitoring dose data which describe at least one dose value which is dependent on the monitoring radiation energy applied to at least a part of the patient's body; and/or
 e) treatment dose data which describe at least one dose value which is dependent on the treatment radiation energy applied to at least a part of the patient's body; and/or
 f) movement indication data which describe a frequency and/or degree of movement of the patient's body; and/or
 g) monitoring dose rate data which describe a monitoring dose applied to the patient's body per unit of time; and/or
 h) treatment dose per unit of time data which describe a treatment dose applied to the patient's body per unit of time.

12. The data processing method according to claim 11, wherein the movement indication data are determined on the basis of at least one of the following:
 a) a vibration measurement of the patient's body;
 b) a vital parameter of the body;
 c) a comparison with preceding monitoring results; and/or
 d) an optical analysis of the movement of the body.

13. The data processing method according to claim 2, wherein the monitoring process involves acquiring images of the patient's body by means of monitoring radiation.

14. The method of claim 1, wherein the radiation energy is an energy applied for the radiation treatment.

15. A computer program embodied on a non-transitory computer readable medium which, when running on a computer or when loaded onto a computer, causes the computer to perform steps for controlling a process of monitoring a position of at least a part of a patient's body during a radiation treatment by means of a computer, the steps comprising:
 a) providing energy data which describe an energy value which is dependent on a radiation energy applied to the patient's body, and
 b) determining control data in accordance with the energy data, wherein the control data are designed to control the time at which monitoring is performed, the time being controlled in accordance with the energy value.

16. A computer on which the computer program according to claim 15 is running or into the memory of which the program according to claim 15 is loaded.

17. A radiation treatment system, comprising:
 a) the computer according to claim 16, which is designed to determine control data on the basis of the energy data provided and to issue the control data in order to control a monitoring device;
 b) a monitoring device, which is designed to monitor the position of at least a part of a patient's body which is to be treated using treatment radiation and designed to be controlled in accordance with the control data; and
 c) a treatment device which is designed to emit the treatment radiation used for the radiation treatment.

18. A non-transient program storage medium on which the computer program of claim 15 is stored.

19. A method for controlling a process of monitoring the position of at least a part of a patient's body during a radiation treatment, the monitoring of the position of at least part of the patient's body being performed by acquiring an image using monitoring radiation applied to the at least part of the patient's body, the method comprising the following steps:
 a) providing an energy value which is dependent on the radiation energy applied to the patient's body; and
 b) controlling the time at which the image is acquired, in accordance with the energy value.

20. A computer program embodied on a non-transitory computer readable medium which, when running on a computer or when loaded onto a computer, causes the computer to perform the steps for controlling a process of monitoring a position of at least a part of a patient's body during a radiation treatment by means of a computer, the monitoring being performed by acquiring an image of at least a part of the patient's body using monitoring radiation, the steps comprising:
 a) providing energy data which describe an energy value which is dependent on a radiation energy applied to the patient's body, and
 b) determining control data in accordance with the energy data, wherein the control data are designed to control the time at which the image is acquired, the time being controlled in accordance with the energy value.

21. A computer on which a computer program is running or into the memory of which the computer program is loaded, the computer program causing the computer to perform the steps for controlling a process of monitoring a position of at least a part of a patient's body during a radiation treatment by means of a computer, the monitoring being performed by acquiring an image of at least a part of the patient's body using monitoring radiation, the steps comprising:
 a) providing energy data which describe an energy value which is dependent on a radiation energy applied to the patient's body, and
 b) determining control data in accordance with the energy data, wherein the control data are designed to control the time at which the image is acquired, the time being controlled in accordance with the energy value.

22. A radiation treatment system, comprising:
 a) the computer according to claim 21, which is designed to determine control data on the basis of the energy data provided and to issue the control data in order to control a monitoring device;
 b) a monitoring device, which is designed to monitor the position of at least a part of a patient's body which is to be treated using treatment radiation and designed to be controlled in accordance with the control data; and
 c) a treatment device which is designed to emit the treatment radiation used for the radiation treatment.

* * * * *